(12) United States Patent
Toshima (10) Patent No.: US 10,632,264 B2
(45) Date of Patent: Apr. 28, 2020

(54) TRANSFUSION APPARATUS AND METHOD FOR DETECTING BUBBLES

(71) Applicant: MINEBEA MITSUMI INC., Kitasaku-gun, Nagano (JP)

(72) Inventor: Toshio Toshima, Kakegawa (JP)

(73) Assignee: MINEBEA MITSUMI INC., Nagano (JP)

( * ) Notice: Subject to any disclaimer, the term of this patent is extended or adjusted under 35 U.S.C. 154(b) by 560 days.

(21) Appl. No.: 15/218,534

(22) Filed: Jul. 25, 2016

(65) Prior Publication Data

US 2017/0028140 A1  Feb. 2, 2017

(30) Foreign Application Priority Data

Jul. 30, 2015 (JP) ................................ 2015-151010

(51) Int. Cl.
*A61M 5/36* (2006.01)
*A61M 5/142* (2006.01)
(Continued)

(52) U.S. Cl.
CPC ........ *A61M 5/365* (2013.01); *A61M 5/14228* (2013.01); *A61M 5/172* (2013.01);
(Continued)

(58) Field of Classification Search
CPC ...... A61M 2205/18; A61M 2205/3331; A61M 2205/3375; A61M 2205/50;
(Continued)

(56) References Cited

U.S. PATENT DOCUMENTS 5,217,355 A * 6/1993 Hyman ............. A61M 5/14228
417/474
5,807,322 A * 9/1998 Lindsey ............ A61M 5/16859
604/65
(Continued)

FOREIGN PATENT DOCUMENTS

CN      103068420 A     4/2013
JP      H05-195959 A    8/1993
(Continued)

OTHER PUBLICATIONS

Notification of Reasons for Refusal dated May 28, 2018 for corresponding Japanese Application No. 2015-151010 and English translation.

(Continued)

*Primary Examiner* — Jason E Flick
(74) *Attorney, Agent, or Firm* — Pearne & Gordon LLP (57) ABSTRACT

A transfusion apparatus according to an embodiment includes a finger-type pump mechanism, the finger-type pump mechanism including a plurality of fingers, the plurality of fingers and a holding member sandwiching a passage composed of a flexible material, the holding member being arranged to face the plurality of fingers in an opposed manner, the finger-type pump mechanism depressing and elastically deforming a side face of the passage by a peristaltic motion reciprocating the plurality of fingers to send a liquid with which the passage is filled, the transfusion apparatus comprising: a pressure sensor provided to at least one of the plurality of fingers or the holding member; and a determination unit that determines presence or absence of bubbles in the passage based on pressure detected by the pressure sensor when a finger is depressing the passage.

10 Claims, 5 Drawing Sheets

(51) Int. Cl.
*G16H 40/63* (2018.01)
*A61M 5/172* (2006.01)

(52) U.S. Cl.
CPC ....... *G16H 40/63* (2018.01); *A61M 2205/103* (2013.01); *A61M 2205/18* (2013.01); *A61M 2205/3317* (2013.01); *A61M 2205/3331* (2013.01); *A61M 2205/3375* (2013.01); *A61M 2205/50* (2013.01); *A61M 2205/502* (2013.01); *A61M 2205/52* (2013.01)

(58) Field of Classification Search
CPC .. A61M 2205/52; A61M 5/172; A61M 5/365; A61M 2205/103; A61M 2205/3317; A61M 2205/502; A61M 5/14228; G06F 19/3406; G16H 40/63
USPC .......................................................... 604/67
See application file for complete search history.

(56) References Cited

U.S. PATENT DOCUMENTS

| | | |
|---|---|---|
| 2003/0214412 A1* | 11/2003 | Ho ................... A61M 5/14228 340/611 |
| 2011/0152772 A1 | 6/2011 | Rotem et al. |
| 2013/0211323 A1 | 8/2013 | Lee |
| 2014/0207057 A1 | 7/2014 | Zhu |

FOREIGN PATENT DOCUMENTS

| | | |
|---|---|---|
| JP | 06-317257 A | 11/1994 |
| JP | 2000-325476 A | 11/2000 |
| JP | 2016-220957 A | 12/2016 |
| WO | 2013/125576 A1 | 8/2013 |

OTHER PUBLICATIONS

Notification of Reasons for Refusal dated Dec. 18, 2018 for corresponding Japanese Application No. 2015-151010 and English translation.

Chinese Office Action for Application No. 201610602208.X, dated Apr. 29, 2019.

Decision to Grant a Patent dated Jun. 25, 2019 for corresponding Japanese Application No. 2015-151010 and English translation.

* cited by examiner

TRANSFUSION APPARATUS AND METHOD FOR DETECTING BUBBLES

CROSS-REFERENCE TO RELATED APPLICATION(S)

The present application claims priority to and incorporates by reference the entire contents of Japanese Patent Application No. 2015-151010 filed in Japan on Jul. 30, 2015.

BACKGROUND OF THE INVENTION

1. Field of the Invention

The present invention relates to a transfusion apparatus and a method for detecting bubbles in the transfusion apparatus.

2. Description of the Related Art

There is disclosed a technique of detecting bubbles generated in a tube (transfusion tube) used for sending a liquid medicine in a medical-use transfusion apparatus. For example, Japanese Laid-open Patent Publication No. 2000-325476 discloses an infusion pump that sends the liquid medicine while sequentially depressing the transfusion tube (peristalsis type) or depressing a member incorporated in a part of the infusion pump (piston type) and, at the same time, detects the presence of bubbles in the liquid medicine to be sent. The infusion pump includes a bubble detector provided with an ultrasonic sensor thus detecting bubbles with accuracy.

However, in the technique described in Japanese Laid-open Patent Publication No. 2000-325476, it is necessary to ensure the exclusive space for arranging the bubble detector provided with the ultrasonic sensor in the transfusion apparatus and hence, there exist problems in terms of the miniaturization of the transfusion apparatus.

The present invention has been made to overcome such problems, and it is an object of the present invention to provide a transfusion apparatus capable of being easily miniaturized, and a method for detecting bubbles, the method being suitable for miniaturizing the transfusion apparatus.

SUMMARY OF THE INVENTION

It is an object of the present invention to at least partially solve the problems in the conventional technology.

A transfusion apparatus according to an embodiment includes a finger-type pump mechanism, the finger-type pump mechanism including a plurality of fingers, the plurality of fingers and a holding member sandwiching a passage composed of a flexible material, the holding member being arranged to face the plurality of fingers in an opposed manner, the finger-type pump mechanism depressing and elastically deforming a side face of the passage by a peristaltic motion reciprocating the plurality of fingers to send a liquid with which the passage is filled, the transfusion apparatus comprising: a pressure sensor provided to at least one of the plurality of fingers or the holding member; and a determination unit that determines presence or absence of bubbles in the passage based on pressure detected by the pressure sensor when a finger is depressing the passage.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, the explanation is specifically made with respect to an embodiment of a transfusion apparatus and a method for detecting bubbles according to the present invention with reference to the accompanying drawings. Here, the present invention is not limited to the embodiment. In the respective drawings, components having identical functions or corresponding to each other are properly given same numerals.

Embodiment

Figure 1:
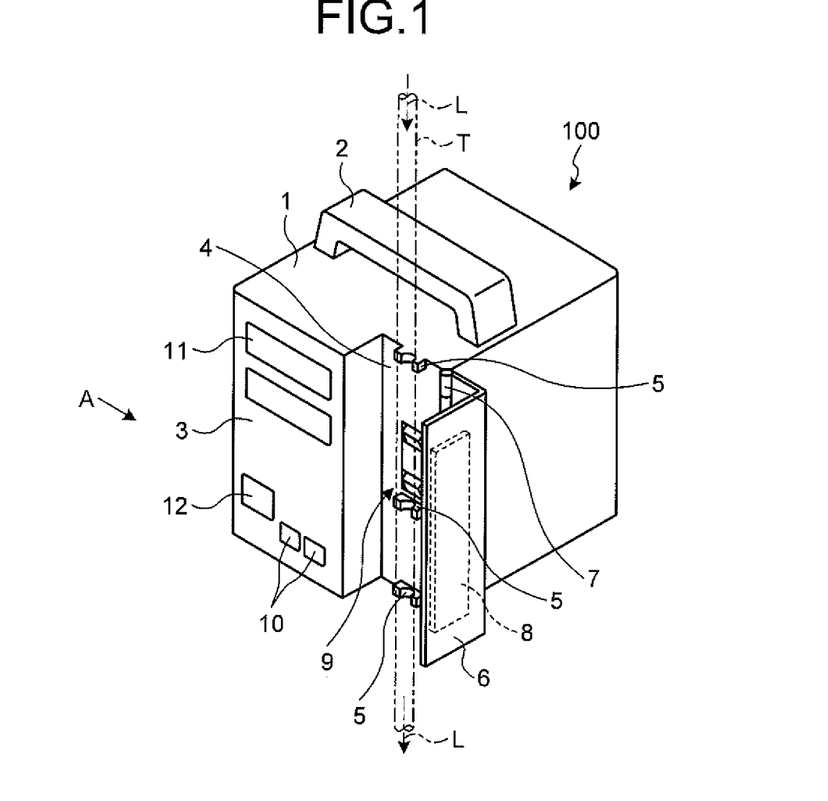
FIG. 1 is a perspective view of a transfusion apparatus according to an embodiment.

FIG. 1 is a perspective view of a transfusion apparatus according to the embodiment of the present invention. This transfusion apparatus 100 is a medical-use transfusion apparatus. The transfusion apparatus 100 has a finger-type pump mechanism described later, and the pump mechanism depresses a transfusion tube T that is a passage composed of a flexible material to send a liquid medicine L with which the transfusion tube T is filled.

The transfusion apparatus 100 includes a housing 1, a carrying-use handle 2 attached to the upper portion of the housing 1, an operation panel 3 with which various kinds of components for operating the transfusion apparatus 100 are provided, a transfusion-tube placing surface 4 on which the transfusion tube T is placed, a transfusion tube guide 5 that guides and holds the transfusion tube T into a predetermined position, a door 6 for covering the transfusion-tube placing surface 4, a hinge 7 that supports the door 6 in an openable manner, a holder plate 8 that is a holding member provided to the inner surface (surface facing the transfusion-tube placing surface 4 in an opposed manner) of the door 6, a finger part 9 exposed from an opening formed in the transfusion-tube placing surface 4, a switch group 10, which is provided to the operation panel 3, including a plurality of buttons for operating the transfusion apparatus 100, a display device 11 for displaying various kinds of information with respect to the transfusion apparatus 100, and an alarm generation device 12 that generates a warning sound. As illustrated in FIG. 1, the finger part 9 is located directly below the transfusion tube T when the transfusion tube T is held by the infusion tube guide 5. Furthermore, the liquid medicine L that is a fluid is sent from an upper side toward a lower side in the vertical direction on the paper on which FIG. 1 is drawn, as indicated by an arrow.

Figure 2:
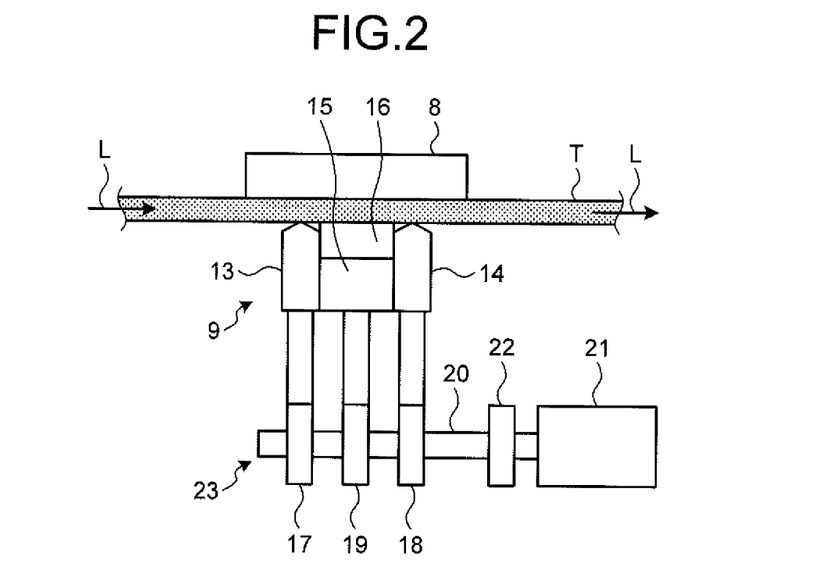
FIG. 2 is a schematic diagram of a part relevant to a finger-type pump mechanism of the transfusion apparatus illustrated in FIG. 1.

FIG. 2 is a schematic diagram of a part relevant to a finger-type pump mechanism of the transfusion apparatus 100. FIG. 2 illustrates a part relevant to a finger-type pump mechanism in a state in which the door 6 is closed, as viewed in the direction indicated by an arrow A in FIG. 1.

The finger part 9 is provided with a plurality of fingers (three fingers in the present embodiment). To be more specific, the finger part 9 is provided with a first finger 13 arranged on the uppermost stream side (left side on the paper on which FIG. 2 is drawn) in the direction in which the liquid medicine L is sent in the transfusion tube T, a second finger 14 arranged on the lowermost stream side (right side on the paper on which FIG. 2 is drawn) in the direction in which the liquid medicine L is sent in the transfusion tube T, and a third finger 15 arranged between the first finger 13 and the second finger 14. Each of the distal end portions of the first finger 13 and the second finger 14 is tapered so that the transfusion tube T is easily blocked. Furthermore, a pressure sensor part 16 is arranged on the distal end portion of the third finger 15. The pressure sensor part 16 is explained later.

The first finger 13, the second finger 14, and the third finger 15 have proximal end portions that are connected to cam members 17, 18, and 19, respectively. The cam members 17, 18, and 19 are configured to be integrally rotatable with a rotational shaft 20. The rotational shaft 20 is connected to the rotational shaft of an electric motor 21 serving as a pump drive source in the transfusion apparatus 100. The electric motor 21 is provided with reduction gears. The rotational shaft 20 includes a rotary position sensor 22 for detecting a rotational position of the electric motor 21. The finger part 9, the cam members 17, 18, and 19, the rotational shaft 20, the electric motor 21, and the rotary position sensor 22 constitute a finger-type pump mechanism 23.

When the electric motor 21 rotates and the rotational shaft 20 rotates about the center axis thereof, the motion direction of the rotational motion of the rotational shaft 20 is changed by the rotational motion of the cam members 17, 18, and 19. This causes the cam members 17, 18, and 19 to reciprocate the first finger 13, the second finger 14, and the third finger 15, respectively, in the direction perpendicular to the extending direction of the transfusion tube T (vertical direction on the paper on which FIG. 2 is drawn). The cam members 17, 18, and 19 have such shapes that can reciprocate the first finger 13, the second finger 14, and the third finger 15, respectively, at desired timings.

The holder plate 8 and the finger part 9 sandwich the transfusion tube T therebetween in a state that the door 6 is closed. As a result, the finger-type pump mechanism 23 depresses and elastically deforms a side face of the transfusion tube T by a peristaltic motion that reciprocates each finger of the finger part 9 in a state that the finger part 9 and the holder plate 8 sandwich the transfusion tube T therebetween thus feeding the liquid medicine L with which the transfusion tube T is filled.

Figure 3:
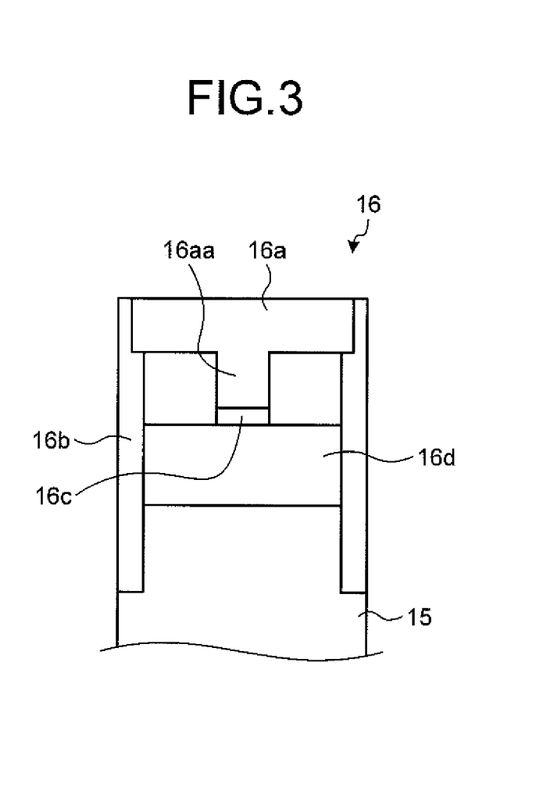
FIG. 3 is a schematic cross-sectional view of a pressure sensor part.

Next, the pressure sensor part 16 is explained. FIG. 3 is a schematic cross-sectional view of the pressure sensor part 16. The pressure sensor part 16 is provided to the third finger 15, and includes a metal sheet 16a having a projection 16aa protruding toward the third finger side thereof, a holding member 16b that holds the metal sheet 16a while holding the pressure sensor part 16 on the third finger 15, a strain gauge 16c serving as a pressure sensor that is attached to the lower side of the projection 16aa of the metal sheet 16a, a pedestal 16d that is arranged between the upper surface of the third finger 15 and the strain gauge 16c and fixed to the holding member 16b.

The strain gauge 16c is constituted of a metal foil resistive element having a predetermined pattern, and is supplied with an electric current via wiring (not illustrated in the drawings). When a pressure is applied to the metal sheet 16a, the metal sheet 16a and the projection 16aa are elastically deformed depending on the pressure and, at the same time, the strain gauge 16c attached to the projection 16aa is elastically deformed, and thus a resistance value of the strain gauge 16c changes in accordance with the deformation of the strain gauge 16c. This allows a change in pressure applied to the metal sheet 16a to be extracted as a change in electric current that flows into the strain gauge 16c.

Figure 4:
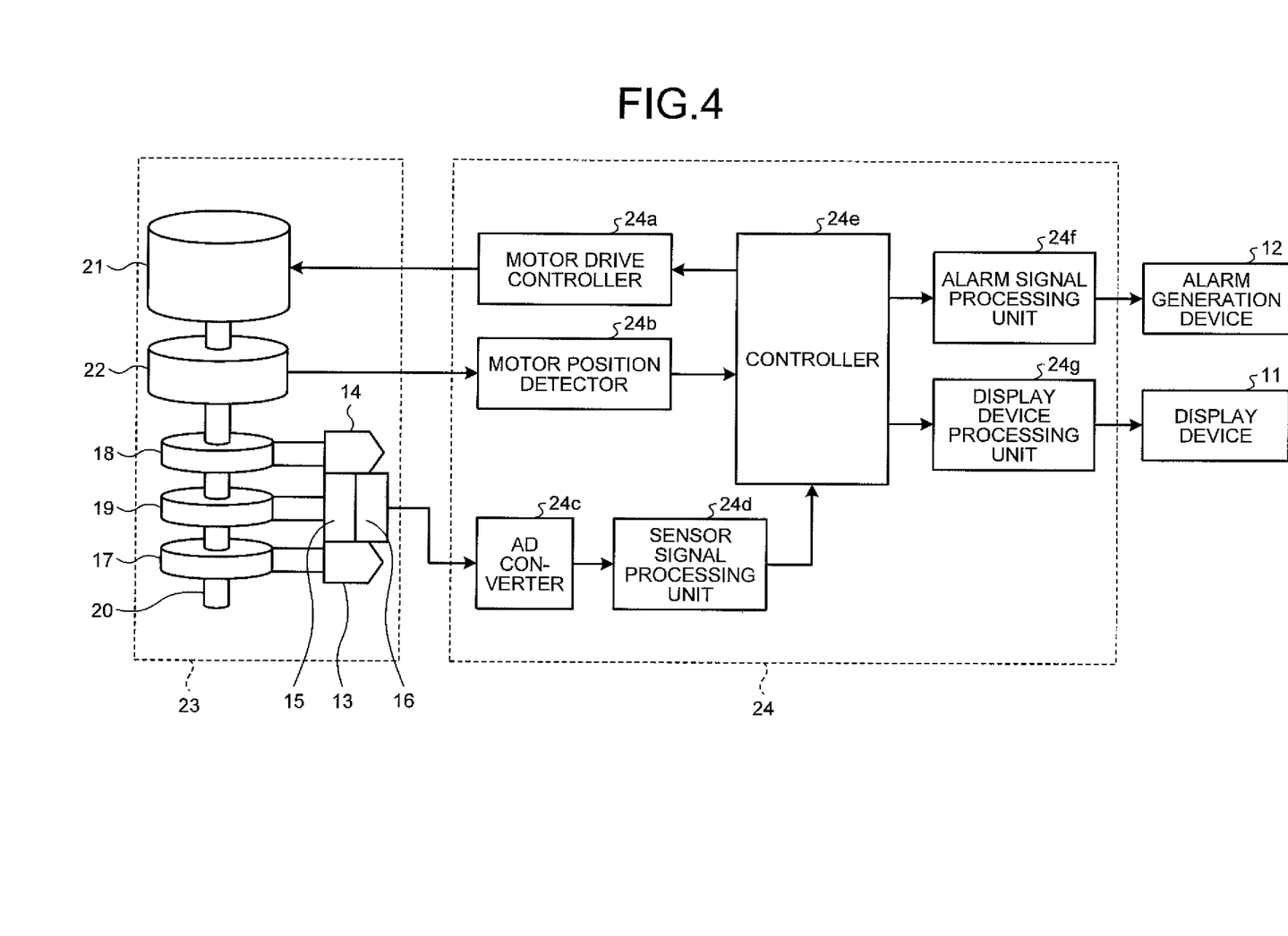
FIG. 4 is a block diagram of a part relevant to the finger-type pump mechanism and a control part of the transfusion apparatus illustrated in FIG. 1.

FIG. 4 is a block diagram of a part relevant to the finger-type pump mechanism 23 and a control part of the transfusion apparatus 100. The detailed explanation with respect to the finger-type pump mechanism 23 is omitted. The transfusion apparatus 100 is controlled by a control device 24.

The control device 24 includes a motor drive controller 24a, a motor position detector 24b, an AD converter 24c, a sensor signal processing unit 24d, a controller 24e, an alarm signal processing unit 24f, and a display device processing unit 24g.

The control device 24 can be implemented by a microcontroller, for example. The microcontroller has a central processing unit (CPU), a read only memory (ROM), a random access memory (RAM), an interface (I/F), and a bus for connecting them to one another. The CPU performs arithmetic processing based on programs and data that are stored in the ROM to achieve the function of each unit. The ROM is a nonvolatile semiconductor memory device that stores programs and data therein. The RAM is a volatile semiconductor memory device that operates as a work area when the CPU executes the programs. The I/F includes the AD converter 24c, and performs the outputting and inputting of data to and from external devices.

Components of the control device 24 are explained below. The motor drive controller 24a drives and controls the electric motor 21 of the finger-type pump mechanism 23 based on a command signal from the controller 24e. The motor position detector 24b detects a rotational position of the electric motor 21 based on a signal output from the rotary position sensor 22 of the finger-type pump mechanism 23, and outputs a motor position detection signal including the information of the rotational position to the controller 24e. The AD converter 24c receives an input voltage corresponding to an electric current that flows through the strain gauge 16c, and converts the input voltage into a digital signal to be output to the sensor signal processing unit 24d. The sensor signal processing unit 24d processes the input digital signal to generate a voltage signal corresponding to the electric current that flows through the strain gauge 16c, and outputs the voltage signal to the controller 24e. The voltage of the voltage signal corresponds to the pressure applied to the metal sheet 16a. Consequently, using the strain gauge 16c, the controller 24e can detect the pressure applied to the pressure sensor part 16 provided to the third finger 15. It is noted that the sensor signal processing unit 24d may adjust the input voltage of the AD converter 24c. For example, when the input voltage includes a noise or the like, the sensor signal processing unit 24d may have a function of removing a value corresponding to the noise, or a function of computation so that the ratio of the voltage signal generated by the sensor signal processing unit 24d to the input voltage of the AD converter 24c becomes a predetermined ratio.

The controller 24e outputs to the motor drive controller 24a, as mentioned above, a command signal for causing the electric motor 21 to be subjected to drive control. Furthermore, the controller 24e receives the motor position detection signal from the motor position detector 24b, and receives the voltage signal from the sensor signal processing unit 24d. In addition, the controller 24e has, as mentioned later, a function as a determination unit for determining the presence or absence of bubbles in the transfusion tube T. The controller 24e outputs, when detecting the presence of bubbles in the transfusion tube T at a step mentioned later, a "false" signal to each of the alarm signal processing unit 24f and the display device processing unit 24g.

The alarm signal processing unit 24f outputs, when accepting the "false" signal from the controller 24e, a command signal to the alarm generation device 12, and causes the alarm generation device 12 to generate the warning sound for notifying of the detection of bubbles. Similarly, the display device processing unit 24g outputs, when accepting the "false" signal from the controller 24e, a command signal to the display device 11, and causes the display device 11 to display characters, symbols, or the like for notifying of the detection of bubbles.

Figure 5A:
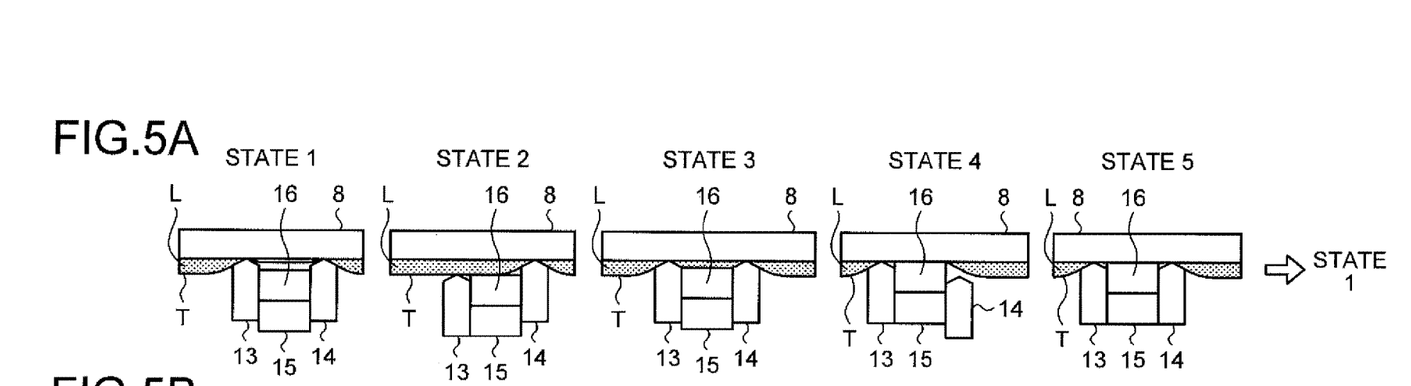
FIGS. 5A, 5B and 5C are views for explaining the operation of the transfusion apparatus illustrated in FIG. 1 and a method for detecting a bubble.
Figures 5B, 5C:
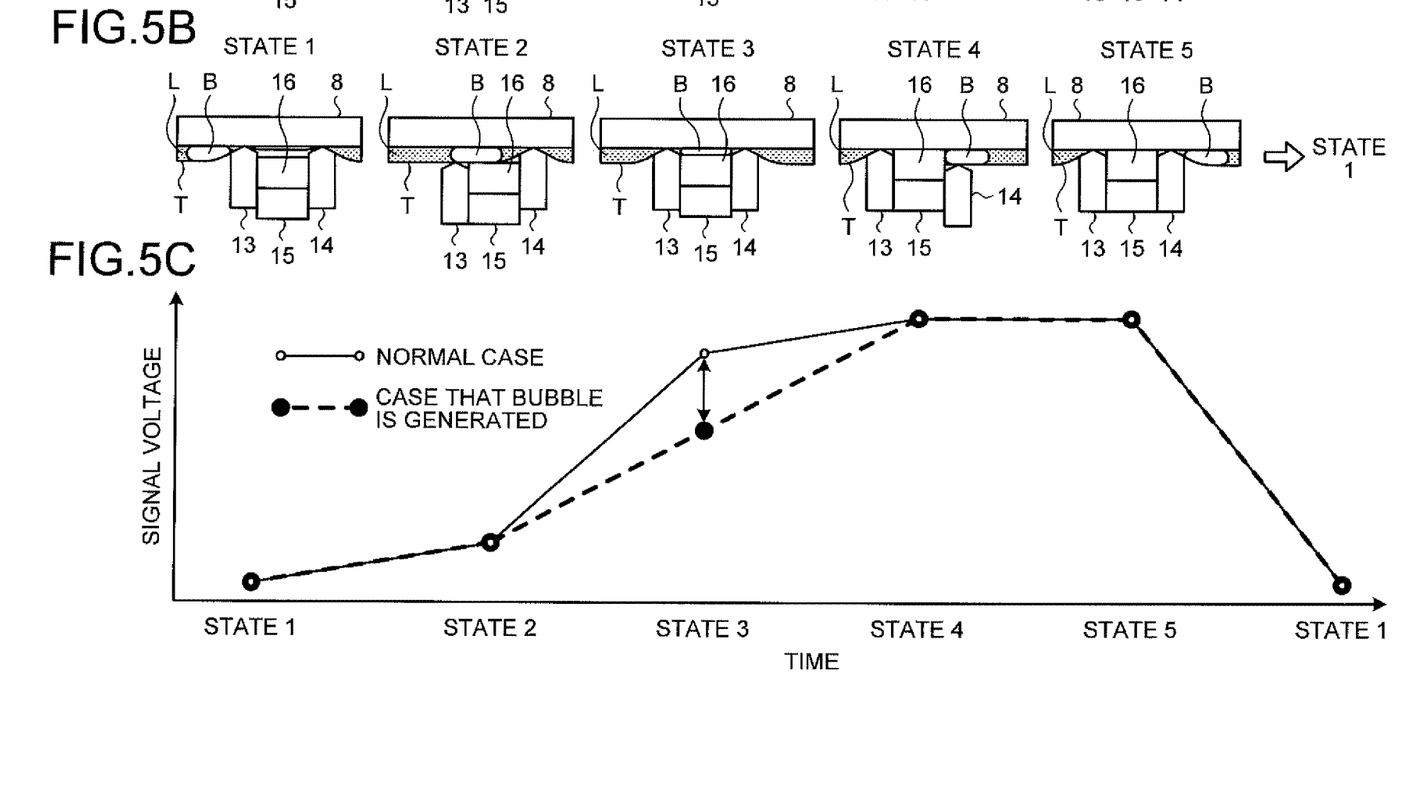

Next, FIG. 5A, FIG. 5B, and FIG. 50 explain the operation of the transfusion apparatus 100 and the method for detecting bubbles. FIG. 5A illustrates a case that bubbles are not generated in the transfusion tube T (normal case), FIG. 53 illustrates a case that bubbles are generated in the transfusion tube T, and FIG. 5C illustrates the voltage (signal voltage) of the voltage signal input to the controller 24e from the sensor signal processing unit 24d.

First of all, FIG. 5A is explained. The finger-type pump mechanism 23 reciprocates each finger of the finger part 9 in a state that the finger part 9 and the holder plate 8 sandwich the transfusion tube T therebetween, and repeatedly performs the peristaltic motion illustrated in the drawings of State 1 to State 5.

State 1 is a state that the first finger 13 and the second finger 14 are simultaneously depressing the side face of the transfusion tube T to block the transfusion tube T. The liquid medicine L is supplied from the upstream side (lower side of FIG. 5). Here, the third finger 15 is in a state of not depressing the side face of the transfusion tube T. Furthermore, the region directly above the third finger 15 in the transfusion tube T is not filled with liquid medicine L. In this case, no pressure is applied to the pressure sensor part 16 provided to the third finger 15, and the voltage signal of a value indicating that no pressure is applied is input to the controller 24e from the sensor signal processing unit 24d (see FIG. 5C).

In State 2 that follows State 1, the first finger 13 retreats to the position at which the first finger 13 does not depress the side face of the transfusion tube T. Consequently, the transfusion tube T blocked by the first finger 13 is brought into an unblocked state, and the liquid medicine L is sent to the region directly above the first finger 13 and the third finger 15 in the transfusion tube T. In this case, a pressure is applied to the pressure sensor part 16 and hence, the voltage signal corresponding to the pressure is input to the controller 24e from the sensor signal processing unit 24d (see FIG. 5C).

In State 3 that follows State 2, the first finger 13 advances toward the side face of the transfusion tube T, the first finger 13 and the second finger 14 simultaneously depress the side face of the transfusion tube T again, causing the transfusion tube T to be blocked. At the same time as above, the third finger 15 advances toward the side face of the transfusion tube T to depress the side face of the transfusion tube T. In this case, the pressure applied to the pressure sensor part 16 becomes higher than that in the case of State 2 and hence, a voltage signal corresponding to the pressure higher than that in the case of State 2 is input to the controller 24e from the sensor signal processing unit 24d (see FIG. 5C). Here, the pressure applied to the pressure sensor part 16 at this time has a value that indicates the internal pressure in the blocked region of the transfusion tube T. A depressing quantity with respect to the transfusion tube T depressed by the third finger 15 at this time may be such extent that the transfusion tube T is slightly deformed. Furthermore, in State 3, the third finger 15 depresses the side face of the transfusion tube T and thereafter, the third finger 15 may once retreat to a position at which the third finger 15 does not depress the side face of the transfusion tube T.

In State 4 that follows State 3, the second finger 14 retreats to the position at which the second finger 14 does not depress the side face of the transfusion tube T and, at the same time, the third finger 15 further advances toward the side face of the transfusion tube T. Consequently, the first finger 13 and the third finger 15 simultaneously depress the side face of the transfusion tube T to block the transfusion tube T. Accordingly, the liquid medicine L with which the region blocked by the first finger 13 and the second finger 14 in State 3 is filled is sent to the downstream side (upper side on the paper on which FIG. 5A is drawn). Here, the pressure applied to the pressure sensor part 16 is the pressure received from the transfusion tube T blocked and the holder plate 8 and hence, the pressure applied to the pressure sensor part 16 becomes higher than that in the case of State 3. Accordingly, a voltage signal corresponding to the pressure higher than that in the case of State 3 is input to the controller 24e from the sensor signal processing unit 24d (see FIG. 5C).

In State 5 that follows State 4, the second finger 14 advances toward the side face of the transfusion tube T, and the first finger 13, the second finger 14, and the third finger 15 simultaneously depress the side face of the transfusion tube T to block the transfusion tube T. Here, the pressure applied to the pressure sensor part 16 is identical with that in the case of State 4 (see FIG. 5C). Thereafter, the third finger 15 retreats to the position at which the third finger 15 does not depress the side face of the transfusion tube T, and the state of the finger-type pump mechanism 23 returns to State 1. Thereafter, repeating the peristaltic motion illustrated in State 1 to State 5 allows the liquid medicine L to be continuously sent.

Next, FIG. 5B is explained. In the same manner as the case of FIG. 5A, the finger-type pump mechanism 23 reciprocates each finger of the finger part 9 in a state that the finger part 9 and the holder plate 8 sandwich the transfusion tube T therebetween, and the peristaltic motion is repeatedly performed in the same manner as the case of FIG. 5A illustrating State 1 to State 5. Here, in the case of FIG. 5B, it is assumed that a bubble B is generated in the transfusion tube T.

In State 1 and State 2 in FIG. 5B, a value of a voltage signal input to the controller 24e is identical with the value of the voltage signal in the case of FIG. 5A (see FIG. 5C). Furthermore, as illustrated in FIG. 5B, the liquid medicine L is, in State 2, sent to the region directly above the first finger 13 and the third finger 15 in the transfusion tube T and, at the same time, the bubble B is moved.

Next, in State 3, the first finger 13 and the second finger 14 simultaneously depress the side face of the transfusion tube T to block the transfusion tube T and, at the same time, the third finger 15 depresses the side face of the transfusion tube T. In this case, the pressure applied to the pressure sensor part 16 is lower than the pressure applied to the pressure sensor part 16 in the case of FIG. 5A and hence, a signal voltage also lowers (see FIG. 5C). This is because the internal pressure becomes lower compared to the case in which only liquid medicine L is filled with the blocked region as in the case of FIG. 5A, because the bubble B that is a gas exists in addition to the liquid medicine L, in the blocked region of the transfusion tube T.

In the subsequent State 4 and State 5 in FIG. 5B, a value of a voltage signal input to the controller 24e is identical with the value of the voltage signal in FIG. 5A (see FIG. 5C). Furthermore, as illustrated in FIG. 5B, the bubble B moves along with the sending of the liquid medicine L.

As explained heretofore, in the transfusion apparatus 100 according to the present embodiment, in a case where the bubble B is generated in the transfusion tube T, the pressure detected by the pressure sensor part 16 (strain gauge 16c) when the third finger 15 is depressing the transfusion tube T changes compared with the case in which bubbles are not generated. Consequently, the controller 24e is capable of determining the presence or absence of bubbles in the transfusion tube T based on the pressure detected by the pressure sensor part 16. In particular, the presence or absence of bubbles is determined based on the pressure detected by the pressure sensor part 16 when the third finger 15 is depressing the transfusion tube T in a state that the first finger 13 and the second finger 14 are blocking the transfusion tube T and hence, it is possible to surely detect bubbles.

Furthermore, in the transfusion apparatus 100 according to the present embodiment, the pressure sensor part 16 is provided to the third finger 15 and hence, a space for the pressure sensor part 16 that is a component for detecting bubbles can also be used as a space for the finger part 9 that is a component required for sending the liquid medicine L. Consequently, it is possible to achieve the miniaturization of the transfusion apparatus 100.

Furthermore, the transfusion apparatus 100 according to the present embodiment does not use an ultrasonic sensor generally used for detecting bubbles but uses a strain gauge that is comparatively inexpensive as a pressure sensor, thus lowering overall costs for the transfusion apparatus 100.

In the control device 24, the controller 24e is capable of determining a timing at which the third finger 15 provided to the pressure sensor part 16 depresses the transfusion tube T (timing at which State 2 changes to State 3) depending on the motor position detection signal input from the motor position detector 24b. Hereinafter, as one example of a determination flow in the transfusion apparatus 100, the explanation is made with respect to a processing flow that determines the presence or absence of bubbles in the transfusion tube T based on the pressure detected by the pressure sensor part 16 at a timing at which the third finger 15 depresses the transfusion tube T.

Figure 6:
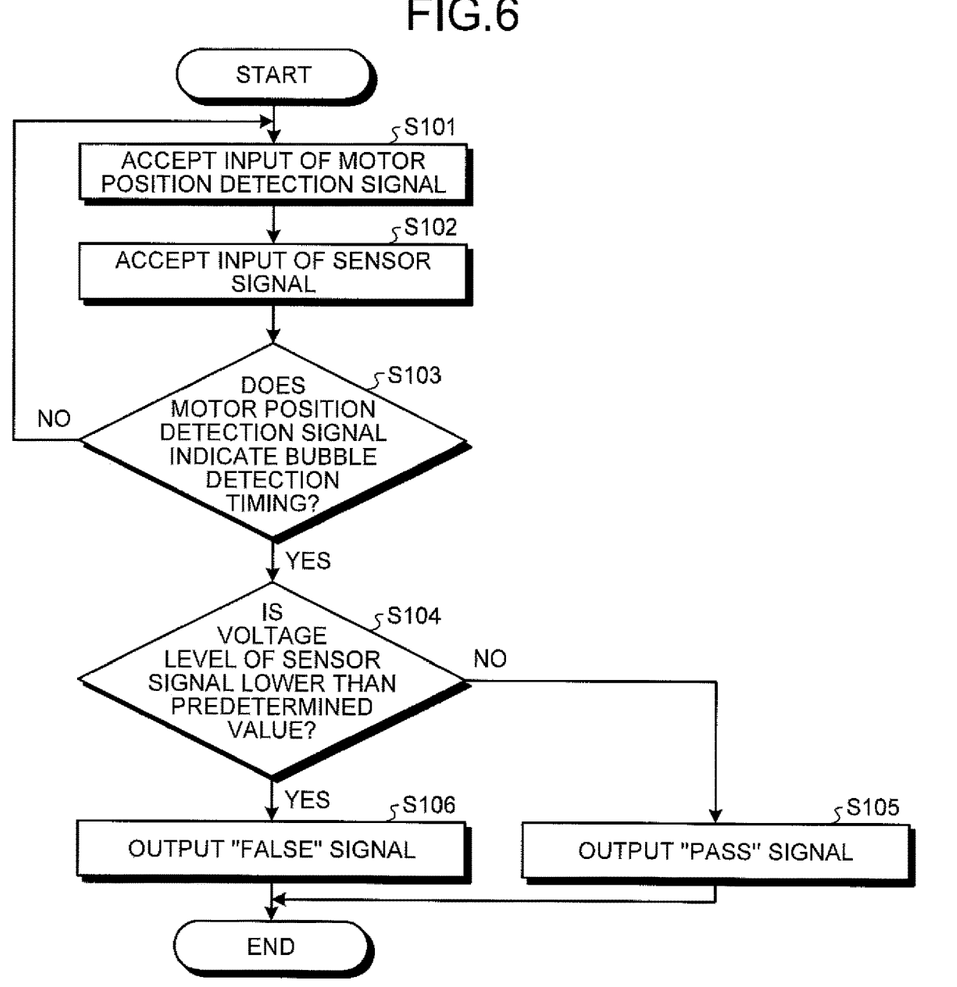
FIG. 6 is a view illustrating one example of a determination flow in the transfusion apparatus illustrated in FIG. 1.

FIG. 6 is a view illustrating one example of a determination flow in the transfusion apparatus illustrated in FIG. 1. First of all, at S101, the controller 24e accepts the input of a motor position detection signal. Subsequently, at S102, the controller 24e accepts the input of a voltage signal (sensor signal) from the sensor signal processing unit 24d.

Subsequently, at S103, the controller 24e determines whether the motor position detection signal indicates a bubble detection timing. To be more specific, the controller 24e determines whether the motor position detection signal that is input to the controller 24e is a signal indicating the rotational position of the electric motor 21 when the third finger 15 is depressing the transfusion tube T (in State 3). When the controller 24e determines that the motor position detection signal does not indicate the bubble detection timing (No at S103), the processing returns to S101. When the controller 24e determines that the motor position detection signal indicates the bubble detection timing (Yes at S103), the processing advances to S104.

Subsequently, at S104, the controller 24e determines whether a voltage level of the sensor signal is lower than a predetermined value. Here, the predetermined value is a value lower than the voltage level in a normal case as illustrated in FIG. 5A, and is a value set to a level at which it is determined that the bubble B is generated in the blocked region in State 3. The predetermined value is, for example, determined through prior experiments depending on a setting value of a depressing quantity of the third finger 15 in State 3, characteristics of the strain gauge 16c, a size of the bubble B to be detected, a type of the liquid medicine L, and the like, and is stored in the ROM in the control device 24.

When the controller 24e determines that the voltage level of the sensor signal is not lower than the predetermined value (No at S104), the processing advances to S105. At S105, the controller 24e outputs a "pass" signal indicating the absence of bubbles to the alarm signal processing unit 24f and the display device processing unit 24g. Then, the processing is terminated. In this case, the display device processing unit 24g may output a command signal to the display device 11 and cause the display device 11 to display characters or symbols indicating the absence of bubbles.

On the other hand, when the controller 24e determines that the voltage level of the sensor signal is lower than the predetermined value (Yes at S104), the processing advances to S106. At S106, the controller 24e outputs a "false" signal indicating that bubbles are detected to the alarm signal processing unit 24f and the display device processing unit 24g. Then, the processing is terminated. The alarm signal processing unit 24f outputs, when accepting the "false" signal output from the controller 24e, the command signal to the alarm generation device 12, and allows the alarm generation device 12 to generate the warning sound for notifying of the detection of bubbles. In the same manner as above, the display device processing unit 24g outputs, when accepting the "false" signal output from the controller 24e, a command signal to the display device 11, and allows the display device 11 to display characters, symbols, or the like for notifying of the detection of bubbles.

Here, in the above-mentioned determination flow, the presence or absence of bubbles in the transfusion tube T is determined based on the pressure detected by the pressure sensor part 16 at the timing that the third finger 15 depresses the transfusion tube T. However, the present invention is not limited to this example. For example, the waveform of the signal voltage in the normal case as illustrated in FIG. 5C in performing the peristaltic motion in State 1 to State 5 is acquired in advance, and stored in the ROM in the control device 24. In this case, it may be possible for the controller 24e to observes a waveform of the signal voltage at the time of performing the peristaltic motion in State 1 to State 5 upon accepting the input from the sensor signal processing unit 24d, and determine that bubbles are generated when the waveform is an abnormal waveform different from the waveform of the signal voltage in the normal case (for example, when a signal voltage lower than the signal voltage in the waveform in the normal case by a predetermined value is observed in the waveform observed).

Furthermore, in the above-mentioned embodiment, although the pressure sensor part 16 provided with the strain gauge 16c is mounted on the third finger 15, such a pressure sensor part may be mounted on the first finger 13 arranged on the uppermost stream side, for example. When the pressure sensor part is mounted on the first finger 13, in the case of State 2 illustrates in FIG. 5, a sensor voltage value changes depending on the presence or absence of bubbles in the transfusion tube T. To be more specific, the presence of bubbles lowers the sensor voltage value. Consequently, for example, it may be possible for the controller 24e to determine the presence of bubbles when the sensor voltage value detected by the pressure sensor part mounted on the first finger 13 is lower than the predetermined value. Furthermore, the pressure sensor part may be provided to each of the first finger 13 and the third finger 15.

In the above-mentioned embodiment, although the finger part 9 is constituted of three fingers, the number of fingers is not limited to three, and may be four or more. In this case also, although a pressure sensor part is provided to at least one finger, the pressure sensor part may be provided to each of a plurality of fingers. In this manner, when a plurality of pressure sensor parts are used, the presence or absence of bubbles is determined based on respective pressures detected by a plurality of pressure sensors, thus improving the detecting accuracy of bubbles. Furthermore, it is possible to determine how many pressure sensors, out of the plurality of pressure sensors, simultaneously detect the pressure lowered and hence, it is also possible to determine the size of the bubbles.

In the above-mentioned embodiment, although each finger of the finger part 9 is reciprocated so that the peristaltic motion in State 1 to State 5 is repeated, the pattern of the peristaltic motion is not limited to the case of State 1 to State 5, and it is possible to perform the peristaltic motion capable of sending a liquid medicine in various kinds of patterns.

The pressure sensor is not limited to a pressure sensor that is provided to the pressure sensor part as in the constitution of the above-mentioned embodiment. The pressure sensor can be provided to a finger part in various aspects, provided that the pressure applied to a finger is capable of being detected when the finger is depressing a transfusion tube. Furthermore, the type of the pressure sensor is not limited to a strain gauge, and various types of pressure sensors, such as a capacitance type sensor, a sensor using a Hall element, a sensor using a resistance film, or a sensor using a piezoelectric element, can be used without limiting a type of sensor, provided that the sensor is capable of detecting pressure.

Figure 7:
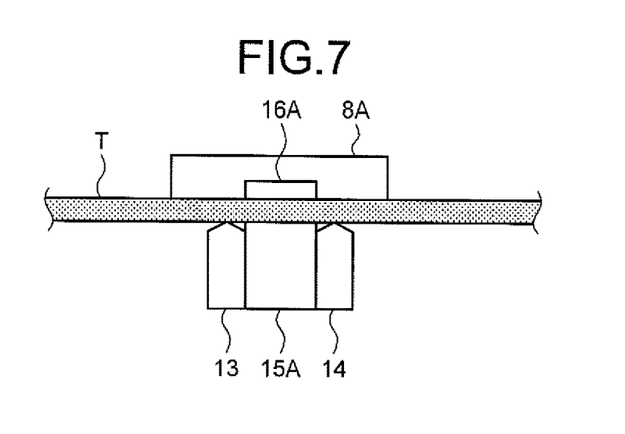
FIG. 7 is a view for explaining a constitution in which the pressure sensor is provided to a holder plate.

In the above-mentioned embodiment, although the pressure sensor is provided to the finger, the pressure sensor may be provided to the holder plate. FIG. V is a view for explaining the constitution in which the pressure sensor is arranged on a holder plate. In the constitution illustrated in FIG. 7, a pressure sensor 16A is buried in a holder plate 8A. The Pressure sensor 16A is, for example, a strain gauge. In this case, the controller 24e is capable of determining the presence or absence of bubbles in the transfusion tube T based on the pressure detected by the pressure sensor 16A when a third finger 15A that is arranged to face the pressure sensor 16A in an opposed manner is depressing the transfusion tube T.

According to the present invention, the pressure sensor is provided to each of the fingers or the holding member, the fingers and the holding member constituting the pump mechanism of the transfusion apparatus, each of the fingers and the holding member being capable of sandwiching the passage therebetween. When the finger is depressing the passage, the presence or absence of bubbles in the passage is determined based on the pressure detected by the pressure sensor and hence, a space for arranging components required for detecting bubbles can also be used as a space for arranging components required for sending the liquid medicine. Accordingly, the advantageous effect that the transfusion apparatus can be miniaturized is achieved.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A transfusion apparatus including a finger-type pump mechanism, the finger-type pump mechanism including a plurality of fingers, the plurality of fingers and a holding member sandwiching a passage composed of a flexible material, the holding member being arranged to face the plurality of fingers in an opposed manner, the finger-type pump mechanism depressing and elastically deforming a side face of the passage by a peristaltic motion reciprocating the plurality of fingers to send a liquid with which the passage is filled, the transfusion apparatus comprising:
   a pressure sensor that is directly held by a third finger out of the plurality of fingers, the third finger being arranged between a first finger and a second finger, the first finger and the second finger being arranged respectively on an uppermost stream side and a lowermost stream side in a direction in which the liquid is sent in the passage, the pressure sensor moving in conjunction with reciprocation of the third finger holding the pressure sensor; and
   a determination unit configured to determine a presence or absence of bubbles in the passage based on pressure detected by the pressure sensor when the third finger holding the pressure sensor is depressing the passage,
   the finger-type pump mechanism is configured to allow the third finger to depress the passage in a state that the first finger and the second finger are simultaneously depressing the passage to block the passage, and
   the determination unit is configured to determine the presence or absence of bubbles in the passage based on the pressure detected by the pressure sensor when the third finger is depressing the passage.

2. The transfusion apparatus according to claim 1, wherein the determination unit is configured to determine the presence of the bubbles in the passage when the pressure detected by the pressure sensor is less than a predetermined value.

3. The transfusion apparatus according to claim 1, wherein the pressure sensor is a strain gauge.

4. The transfusion apparatus according to claim 1, wherein the determination unit is configured to determine whether the third finger holding the pressure sensor is depressing the passage or not based on information of a rotational position of a motor that reciprocates the third finger holding the pressure sensor, and determine the presence or absence of the bubbles in the passage based on pressure detected by the pressure sensor at the time when it is determined that the third finger holding the pressure sensor is depressing the passage.

5. The transfusion apparatus according to claim 4, further comprising a rotary position sensor that detects the rotational position of the motor and outputs a signal including the information of the detected rotational position of the motor.

6. A method of using the transfusion apparatus according to claim 1 to detect the presence or absence of bubbles in the passage, the method comprising: determining the presence or absence of bubbles in the passage based on pressure detected by the pressure sensor when the third finger is depressing the passage.

7. The method according to claim 6, the method comprising: depressing, by the third finger, the passage in a state that the first finger and the second finger are simultaneously depressing the passage to block the passage, and determining the presence or absence of bubbles based on the pressure detected by the pressure sensor when the third finger is depressing the passage.

8. A transfusion apparatus including a finger-type pump mechanism, the finger-type pump mechanism including a plurality of fingers, the plurality of fingers and a holding member sandwiching a passage composed of a flexible material, the holding member being arranged to face the plurality of fingers in an opposed manner, the finger-type pump mechanism depressing and elastically deforming a side face of the passage by a peristaltic motion reciprocating the plurality of fingers to send a liquid with which the passage is filled, the transfusion apparatus comprising:

a pressure sensor that is directly held by a first finger out of the plurality of fingers and moves in conjunction with reciprocation of the first finger holding the pressure sensor; and a determination unit configured to determine a presence or absence of bubbles in the passage based on pressure detected by the pressure sensor when the first finger holding the pressure sensor is depressing the passage, wherein the first finger is arranged on an uppermost stream side in a direction in which the liquid is sent in the passage, the finger-type pump mechanism is configured to allow the first finger to depress the passage in a state that a second finger is depressing the passage to block the passage, the second finger being arranged on an lowermost stream side in the direction in which the liquid is sent in the passage, and the determination unit is configured to determine the presence or absence of bubbles in the passage based on the pressure detected by the pressure sensor when the first finger is depressing the passage.

9. The transfusion apparatus according to claim 8, wherein the determination unit is configured to determine whether the first finger is depressing the passage or not based on information of a rotational position of a motor that reciprocates the first finger, and determine the presence or absence of the bubbles in the passage based on pressure detected by the pressure sensor at the time when it is determined that the first finger holding is depressing the passage.

10. The transfusion apparatus according to claim 9, further comprising a rotary position sensor that detects the rotational position of the motor and outputs a signal including the information of the detected rotational position of the motor.

* * * * *